United States Patent [19]

Yazawa et al.

[11] Patent Number: 5,403,939
[45] Date of Patent: * Apr. 4, 1995

[54] PROCESS FOR PRODUCTION OF 2-ACETYLBENZO[B]THIOPHENE

[75] Inventors: Naoto Yazawa; Yoshinori Saito; Hidetaka Hiyoshi, all of Shizuoka, Japan

[73] Assignee: Takeda Chemical Industries, Ltd., Tokyo, Japan

[*] Notice: The portion of the term of this patent subsequent to Nov. 30, 2010 has been disclaimed.

[21] Appl. No.: 118,184

[22] Filed: Sep. 9, 1993

Related U.S. Application Data

[62] Division of Ser. No. 997,932, Dec. 29, 1992, Pat. No. 5,266,705.

[30] Foreign Application Priority Data

Nov. 20, 1992 [JP] Japan .................. 4-335205

[51] Int. Cl.[6] .......................................... C07D 333/56
[52] U.S. Cl. ........................................ 549/57; 549/64
[58] Field of Search ................... 549/57, 64; 568/68, 568/67, 63

[56] References Cited

U.S. PATENT DOCUMENTS

| | | | |
|---|---|---|---|
| 2,456,588 | 12/1948 | Loverde | 260/609 |
| 2,634,201 | 4/1953 | Mowry | 71/2.5 |
| 3,669,956 | 6/1972 | Borck et al. | 260/239 BF |
| 4,490,532 | 12/1984 | Harris | 546/294 |
| 4,664,693 | 5/1987 | Bird et al. | 71/88 |
| 5,169,961 | 12/1992 | Dickman | 549/57 |

FOREIGN PATENT DOCUMENTS 5-155881 6/1993 Japan .

OTHER PUBLICATIONS

Advanced Organic Chemistry, 2nd Edition, "Reaction, Mechanisms, and Structure", Jerry March.
Heterocycles, vol. 26, No. 10 (Oct. 1, 1987); "A Novel Synthesis of Benzofuran and Related Compounds".
Dickinson et al., "Condensed Thiophen Ring systems"
(List continued on next page.)

*Primary Examiner*—Allen J. Robinson
*Assistant Examiner*—Deborah Lambkin
*Attorney, Agent, or Firm*—Foley & Lardner

[57] ABSTRACT

A process for production of 2-acetylbenzo[b]thiophene represented by the formula (I):

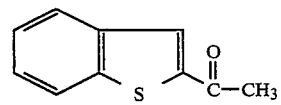

comprising the steps of:
(1) reacting 2-halogenobenzaldehyde represented by the formula (II):

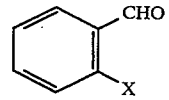

wherein X represents a halogen atom, with a compound represented by the formula (III):

$H_iS_jM_k$ wherein M represents an alkali metal, i represents zero or 1, j represents an integer of at least 1, and k represents an integer of 1 or 2, and preferably also with sulfur; and
(2) reacting the reaction product with a monohalogenoacetone represented by the formula (IV)

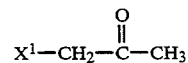

wherein $X^1$ represents a halogen atom.

3 Claims, No Drawings

OTHER PUBLICATIONS

Part VII, Stability of 3-Benzo[b]-thienyl-Lithium, J. Chem. Soc. Commun., pp. 3447–3454 (1971).

Martynoff, *Comptes Rendus,* vol. 234, 1952, pp. 736–738.

Dore et al., *Tetrahedron,* vol. 28, No. 9, 1972, pp. 2553–2573.

Hsiao et al., *Synthetic Communications,* vol. 20, No. 11, 1990, pp. 1687–1695.

European Search Report (Mar. 1994).

Advanced Organic Chemistry, Fourth Edition, Jerry March (II)(1992).

CA Previews 93:389251, 'Prep of Benzo Thiophenes . . .' Kagano et al (1993).

PROCESS FOR PRODUCTION OF 2-ACETYLBENZO[B]THIOPHENE

This application is a divisional of Ser. No. 07/997,932, filed Dec. 29, 1992, now U.S. Pat. No. 5,266,705.

BACKGROUND OF THE INVENTION

1. Field of the Invention

The present invention relates to a process for production of 2-acetylbenzo[b]thiophene, which is useful as an intermediate for the synthesis of an antiinflammatory agent, Zileuton.

2. Related Art

As a process for production of 2-acetylbenzo[b]thiophene, a process comprising reacting benzo[b]thiophene with a strong base such as butyl lithium, followed by reaction with acetylchloride is described in J. Chem. Soc. Comun., 3447 (1977). In this process, however, the reaction with butyllithium must be carried out at a low temperature and therefore an operation is industrially difficult, and moreover the starting material, benzo[b]thiophene is expensive.

Comptes rendus, vol. 234, 736 describes a process for production of 2-acetylbenzo[b]thiophene by reacting 2-mercaptobenzaldehyde with chloroacetone. However, in this process, the starting material, 2-mercaptobenzaldehyde is difficult to synthesize, and unstable, and therefore handling the same is not convenient.

SUMMARY OF THE INVENTION

Accordingly, the present invention provides a process for production of 2-acetylbenzo[b]thiophene, using an industrially applicable operation and industrially available starting material.

More specifically, the present invention provides a process for production of 2-acetylbenzo[b]thiophene represented by the formula [I]:

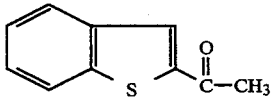

comprising the steps of:

(1) reacting 2-halogenobenzaldehyde represented by the formula (II):

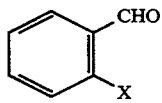

wherein X represents a halogen atom, with a compound represented by the formula (III):

wherein M represents an alkali methal, i represents zero or 1, j represents an integer of at least 1, and k represents an integer of 1 or 2; and (2) reacting the reaction product with a monohalogenoacetone represented by the formula (IV):

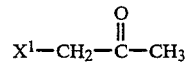

wherein $X^1$ represent a halogen atom.

The present invention further provides a process for production of 2-acetylbenzo[b]thiophene comprising the steps of:

(1) reacting 2-halogenobenzaldehyde (II) with a compound represented by the formula (III) and sulfur; and (2) reacting the reaction product with a monohalogenoacetone (IV).

PREFERRED EMBODIMENT FOR CARRYING OUT THE INVENTION

The present process is preferably carried out in an aprotic polar solvent, such as N-methypyrrolidone, N-octylpyrrolidone, 1,3-dimethylimidazolidinone, diethylacetamide, dimethylacetamide, dimethylformamide, dimethylsulfoxide, sulforan, tetramethylurea, hexamethylphosphoric triamide, N-methyl-N-phenylformamide or the like, or mixtures thereof. Moreover, according to the present invention, a mixed solvent comprising one or more than one of the above-mentioned aprotic polar solvents and other inert solvents miscible with the aprotic polar solvent can be used. Such solvents include benzene, toluene, xylenes, chlorobenzene, dichlorobenzenes and the like.

The amount of solvent is not critical as long as it provides a viscosity that allows agitation of the reaction mixture, such as a slurry, but should preferably be 100 ml to 3000 ml per 1 mole of 2-halogenobenzaldehyde.

In an embodiment (the first embodiment) of the first reaction (1), 2-halogenobenzaldehyde represented by the above-mentioned formula (II) is reacted with a compound represented by the above-mentioned formula (III). In the formula (II), the halogen as the substituent X may be any halogen, such as fluorine, chlorine, bromine or iodine, but preferably X represents chlorine atom, because chlorobenzaldehyde is industrially available and not expensive. The compound represented by the above-mentioned formula (III) is, for example, potassium sulfide ($K_2S$), sodium sulfide ($Na_2S$), potassium hydrogen sulfide (KSH), sodium hydrogen sulfide (NaSH), potassium polysulfide, sodium polysulfide, or the like.

The amount of compound (III) is preferably 0.5 to 10 moles and more preferably 1 to 3.5 moles, per 1 mole of 2-halogenobenzaldehyde (II).

In the formula (III) the integer j is for example 1 to 10, and usually 1 to 6.

The first reaction is usually carried out at a temperature between 0° C. and the boiling point of the solvent used, and preferably between 0° C. and 50° C. The end point of the reaction may be confirmed by the disappearance of 2-halogenobenzaldehyde as determined by gas chromatography, and usually the reaction time is about 3 to 24 hours.

The first reaction may be carried out by adding 2-halogenobenzaldehyde (compound II) to a compound represented by the formula (III), or by adding the compound (III) to 2-halogenobenzaldehyde (II), but preferably by adding 2-halogenobenzaldehyde (II) to compound (III).

In another embodiment (the second embodiment) of the first reaction (1), 2-halogenobenzaldehyde represented by the formula (II) is reacted with a compound represented by the formula (III) and sulfur. The compound (II), the compound (III), amounts of the compounds (II) and (III), and other conditions such as the order for adding reactants are the same as those described for the first embodiment of the first reaction.

In the second embodiment, the compound (III) and sulfur are preferably mixed in an aprotic polar solvent at a temperature between a room temperature and about 50° C. for 0.5 to 3 hours with agitation, prior to reaction with the compound (II). This reaction provides a polysulfide of metal M.

Although the present invention may use either the first embodiment or the second embodiment in the first reaction, the second embodiment provides the final product 2-acetylbenzo[b]thiophene, in a yield higher than the first embodiment, and therefore the second embodiment is preferable.

In the second reaction, the product of the first reaction is reacted with a monohalogenoacetone represented by the above-mentioned formula (IV).

In the formula (IV), $X^1$ may be any halogen, such as fluorine, chlorine, bromine or the like, but preferably, the monohalogenoacetone is monochloroacetone or monobromoacetone.

The amount of monohalogeneacetone is usually 0.5 to 10 moles and preferably 1 to 2 moles per 1 mole of 2-halogenobenzaldehyde.

Since the second reaction is exothermic, during the reaction, the reaction mixture is preferably cooled to maintain a temperature between 0° C. and 50° C. The reaction time is usually 1 to 16 hours depending on the reactants, solvent, reaction temperature and other conditions.

It is considered that the first reaction provides 2-mercaptobenzaldehyde as a main product, and in an embodiment of the present invention, the 2-mercaptobenzaldehyde is once recovered from the reaction mixture of the first reaction, and the isolated 2-mercaptobenzaldehyde is used in the second reaction.

However, since 2-mercaptobenzaldehyde is unstable and difficult to isolate in a good yield, according to a preferred embodiment of the present invention, monohalogenoacetone is added to the reaction mixture of the first reaction after completing the first reaction, and then the second reaction is carried out in the same reaction medium and reaction vessel as the first reaction. Alternatively, the reaction mixture of the first reaction may be added to monohalogenoacetone.

In the embodiment wherein the first and second reactions are carried out in the same reaction medium without isolating 2-mercaptobenzaldehyde the total reaction time is usually 4 to 43 hours.

The final product, 2-acetylbenzo[b]thiophene can be obtained with a high degree of purity by crystallization from a mixture of cyclohexane or an alcohol, such as isopropanol, and water, or by distillation.

According to the present invention, 2-acetylbenzo[b]thiophene can be industrially produced using stable and inexpensive starting materials, by a simple operation.

EXAMPLES

The present invention is described in detail by the Example hereinafter.

Example 1

To a 200 ml four-necked flask, equipped with a stirrer, a thermometer and a reflux condenser, were added 9.63 g (68 m moles) of sodium trisulfide and 50 ml of N,N-diethylacetamide, and the mixture was stirred at room temperature for one hour. To the reaction mixture was dropwise added 5.50 g (60 m moles) of chloroacetone, and the reaction mixture was stirred at room temperature for 16 hours. After finishing the reaction, 100 ml of diethyl ether and 100 ml of water were added to the reaction mixture, and the pH value of the aqueous layer was adjusted to higher than 11 with a sodium hydroxide aqueous solution, and extracted with diethyl ether. The diethyl ether extract was twice washed with water, and concentrated under a reduced pressure to obtain 7.0 g of 2-acetylbenzo[b]thiophene (yield 79%). The purity of the product is 95% as determined by gas chromatography.

Example 2 to 5

The same procedure as described in Example 1 was repeated except that the compound (III) and reaction medium (solvent) were changed as shown in Table 1.

TABLE 1

| Example No. | 2-Halogeno-benzaldehyde | Compound (III) | Solvent | Yield (%) |
|---|---|---|---|---|
| 2 | 2-chloro-benzaldehyde | Sodium sulfide | N-methyl-pyrrolidone | 58 |
| 3 | 2-chloro-benzaldehyde | Potassium sulfide | N-methyl-pyrrolidone | 60 |
| 4 | 2-chloro-benzaldehyde | Sodium tetra-sulfide | N-methyl-pyrrolidone | 75 |
| 5 | 2-chloro-benzaldehyde | Sodium hydrogensulfide | N-methyl-pyrrolidone | 57 |

Example 6

To a 200 ml four-necked flask, equipped with a stirrer, a thermometer and a reflux condenser, were added 11.7 g (150 m moles) of anhydrous sodium sulfide, 3.2 g (100 m moles) of sulfur and 100 ml of N-methylpyrrolidone, and the mixture was stirred at room temperature for one hour. To the reaction mixture was dropwise added 14.1 g (100 m moles) of 2-chlorobenzaldehyde, and the mixture was stirred at room temperature for 12 hours. To the reaction mixture, was dropwise added 11.1 g (120 m moles) of chloroacetone with cooling, and the reaction mixture was stirred at room temperature for 6 hours. After finishing the reaction, 100 ml of diethyl ether and 100 ml of water were added to the reaction mixture, and pH value of the aqueous layer was adjusted to higher than 11 with a sodium hydroxide aqueous solution, and extracted with diethyl ether. The diethyl ether extract was washed twice with water, and the diethyl ether layer was concentrated under a reduced pressure to obtain 13.0 g of 2-acetylbenzo[b]thiophene (yield 74%). Purity of the product was 95% as determined by gas chromatography.

Example 7

The same procedure as described in Example 6 was repeated except that sulfur was not added. 8.6 g of 2-acetylbenzo[b]thiophene was obtained (yield 51%). The purity of the product was 95% as determined by gas chromatography.

Examples 8 to 14

The same procedure as described in Example 6 was repeated except that 2-halogenobenzaldehyde, the compound (III)+ sulfur, and the reaction medium (solvent) shown in Table 2 were used.

TABLE 2

| Example No. | 2-Halogeno-benzaldehyde | Compound (III) + sulfur | Solvent | Yield (%) |
|---|---|---|---|---|
| 8 | 2-chloro-benzaldehyde | sodium sulfide + sulfur | 1,3-dimethyl imidazolidinone | 76 |
| 9 | 2-chloro-benzaldehyde | sodium sulfide + sulfur | N,N-diethyl acetamide | 91 |
| 10 | 2-chloro-benzaldehyde | sodium sulfide + sulfur | N,N-dimethyl formamide | 71 |
| 11 | 2-chloro-benzaldehyde | sodium sulfide + sulfur | dimethyl sulfoxide | 74 |
| 12 | 2-chloro-benzaldehyde | sodium sulfide + sulfur | N,N-dimethyl acetamide | 78 |
| 13 | 2-bromo-benzaldehyde | sodium sulfide + sulfur | N-methyl-pyrrolidone | 60 |
| 14 | 2-fluoro-benzaldehyde | sodium sulfide + sulfur | N-methyl-pyrrolidone | 66 |

Example 15

The same procedure as described in Example 6 was repeated except that a mixture of N,N-diethylacetamide and toluene (1:1 by volume) was used in place of N-methyl pyrrolidone and the reaction temperature was 60° C. As a result, the yield of 2-acetylbenzo[b]thiophene was 89%.

We claim:

1. A process for production of 2-acetylbenzo[b]thiophene represented by the formula (I):

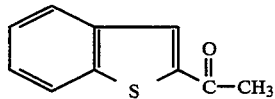

comprising the steps of:
(1) reacting 2-halogenobenzaldehyde represented by the formula (II):

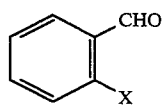

wherein X represents a halogen atom, with a compound represented by the formula (III):

$H_iS_jM_k$ wherein M represents an alkali metal, i represents zero or 1, j represents 1, and k represents an integer of 1 or 2; and (2) reacting the reaction product with a monohalogenoacetone represented by the formula (IV):

wherein $X^1$ represents a halogen atom, without isolation of the intermediate produced by step (1), the first and second reactions being carried out in an aprotic polar solvent.

2. A process according to claim 1, wherein the first reaction (1) and the second reaction (2) are sequentially carried out in the same reaction vessel without isolating the intermediate compound from the first reaction.

3. A process according to claim 1, wherein the aprotic polar solvent is N,N-diethylacetamide or N-methylpyrrolidone.

* * * * *